(12) United States Patent
Zereshkian

(10) Patent No.: US 11,752,232 B2
(45) Date of Patent: Sep. 12, 2023

(54) PERSONALIZED FORCED AIR PURIFIER

(71) Applicant: Gholam Hossein Zereshkian, Richmond Hill (CA)

(72) Inventor: Gholam Hossein Zereshkian, Richmond Hill (CA)

( * ) Notice: Subject to any disclaimer, the term of this patent is extended or adjusted under 35 U.S.C. 154(b) by 149 days.

(21) Appl. No.: 17/111,351

(22) Filed: Dec. 3, 2020

(65) Prior Publication Data

US 2022/0176003 A1   Jun. 9, 2022

(51) Int. Cl.
  *A61L 9/20* (2006.01)
  *A61L 9/22* (2006.01)
  *A62B 18/00* (2006.01)

(52) U.S. Cl.
  CPC ........ *A61L 9/20* (2013.01); *A61L 9/22* (2013.01); *A62B 18/006* (2013.01); *A61L 2209/111* (2013.01); *A61L 2209/134* (2013.01); *A61L 2209/14* (2013.01); *A61L 2209/15* (2013.01)

(58) Field of Classification Search
  CPC ........ A61L 9/20; A61L 9/22; A61L 2209/111; A61L 2209/12; A61L 2209/133; A61L 2209/14; A61L 2209/134; A61L 2209/15; A61L 2209/213; A61L 2209/22; A62B 18/006; A62B 18/02; A62B 18/025; A62B 18/08; A62B 23/02; A62B 9/003; A62B 18/10; G06F 3/147; G09G 2380/08; B01D 46/0028; B01D 46/0002; B01D 2279/40; B01D 50/60; B01D 2275/403; B01D 46/0035; B01D 47/024; B03C 1/30; B03C 1/0335; B03C 2201/20; B03C 1/035; B03C 1/0332; B03C 1/28; C02F 1/4606; C02F 1/46109; C02F 1/461; C02F 2001/46133; C02F 2303/04

See application file for complete search history.

(56) References Cited

U.S. PATENT DOCUMENTS

| | | | | |
|---|---|---|---|---|
| 5,678,576 | A * | 10/1997 | Nazaroff | B01D 46/64 131/331 |
| 8,147,302 | B2 * | 4/2012 | Desrochers | F24F 3/044 702/50 |
| 10,946,321 | B1 * | 3/2021 | Hamidzai | B01D 46/0028 |
| 2002/0057021 | A1 * | 5/2002 | Tanaka | H01L 21/67386 307/116 |
| 2009/0004047 | A1 * | 1/2009 | Hunter | A61L 9/205 422/4 |

(Continued)

FOREIGN PATENT DOCUMENTS

| | | | | |
|---|---|---|---|---|
| CN | 100579585 | C * | 1/2010 | A61L 9/22 |
| CN | 203886344 | U * | 10/2014 | |

(Continued)

*Primary Examiner* — Xiuyu Tai

(74) *Attorney, Agent, or Firm* — Nasser Ashgriz; UIPatent Inc.

(57) ABSTRACT

The present invention is a portable personalized air purifier intended to be attached to the belt or to the neck of a user. Purified air is generated by filtering, electrochemically, and UV LED treating of a polluted air. Polluted air is forced through a filter into ionized water, which absorbs particles and kills possible air born bacteria. The UV LED disinfects the polluted air. The device further balances the humidity of the air and delivers healthy air towards the face of the user through a mask.

7 Claims, 4 Drawing Sheets

(56) References Cited

U.S. PATENT DOCUMENTS

| | | | | |
|---|---|---|---|---|
| 2016/0058901 A1* | 3/2016 | Bender | ................ | C01B 11/024 |
| | | | | 423/477 |
| 2017/0087499 A1* | 3/2017 | Combs | ............... | B01D 46/0001 |
| 2018/0154297 A1* | 6/2018 | Maletich | .................. | F24F 3/16 |
| 2019/0126202 A1* | 5/2019 | Rao | ...................... | B01D 53/885 |
| 2019/0128553 A1* | 5/2019 | Hilbig | ...................... | F24F 1/00 |
| 2021/0115494 A1* | 4/2021 | Reeslev | .................. | C12Q 1/34 |

FOREIGN PATENT DOCUMENTS

| | | | | | |
|---|---|---|---|---|---|
| CN | 104507581 | A | * | 4/2015 | ............... B03C 3/08 |
| CN | 207599879 | U | * | 7/2018 | |
| CN | 208113001 | U | * | 11/2018 | |
| CN | 108952913 | A | * | 12/2018 | |
| CN | 112843410 | A | * | 5/2021 | |
| DE | WO 2020178153 | A1 | * | 9/2020 | |
| EP | 0328782 | A1 | * | 8/1989 | |
| ES | 2331806 | T3 | * | 1/2010 | ............... A61L 9/22 |
| JP | H10180139 | A | * | 7/1998 | |
| JP | 2004073929 | A | * | 3/2004 | ........... F24F 3/1423 |
| JP | 2004184012 | A | * | 7/2004 | ........... F24F 3/1423 |
| JP | 2007317634 | A1 | * | 12/2007 | |
| JP | 2008221174 | A | * | 9/2008 | |
| JP | 2017217981 | A | * | 12/2017 | |
| KR | 20100005971 | A | * | 1/2010 | |
| KR | 20160054731 | A | * | 5/2016 | |
| WO | WO-0247152 | A1 | * | 6/2002 | ....... H01L 21/67017 |
| WO | WO-2011059196 | A2 | * | 5/2011 | ............. F24F 6/043 |

\* cited by examiner

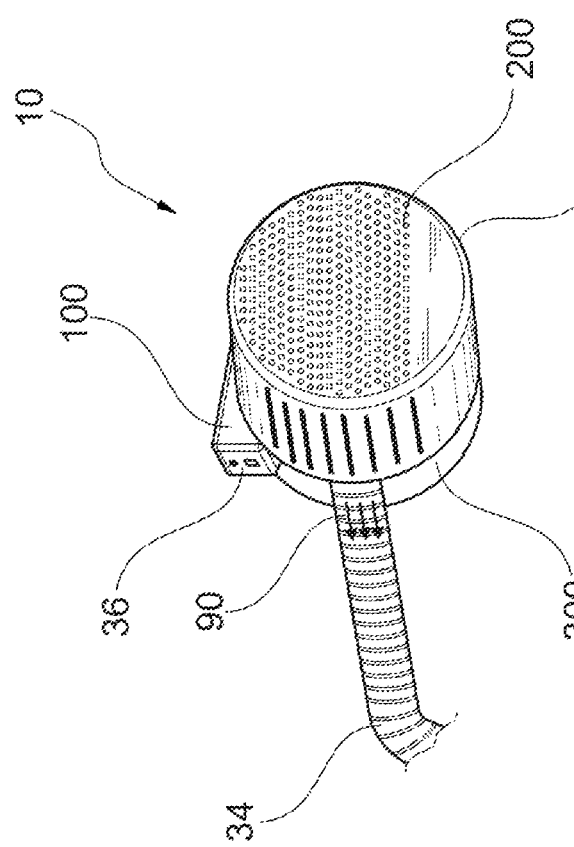
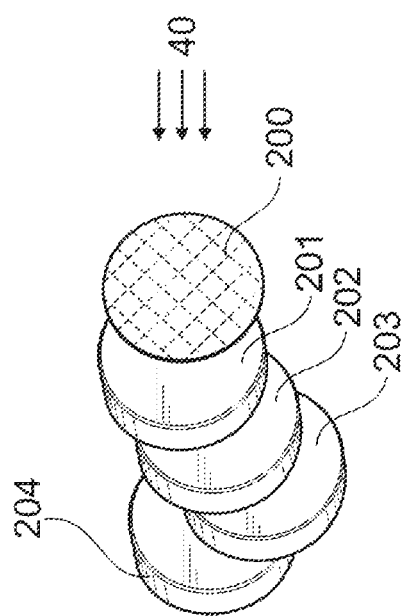
Fig. 1A
Fig. 1B

PERSONALIZED FORCED AIR PURIFIER

FIELD OF THE INVENTION

The present invention relates in general to the field of air purifiers, and in particular to a personalized forced air purifier system and mask.

BACKGROUND OF THE INVENTION

A wide variety of face masks have been developed to protect people from polluted particulate matter and dust. Most of the dust masks have been developed to protect people from larger particulate matters such as sand, wood dust, metal dust or the like. Many filtering masks are designed for removing particles as well as some gasses that may include bacteria or harmful viruses. Filtered masks in the market are not efficient and need high intake pressure, which makes using them difficult, especially for the elderly. These masks are not convenient and they usually cover most of the face. Additionally, they tend to be cumbersome and expensive to manufacture and purchase.

During a pandemic, a personal air purifier that can capture bacteria and virus particles and prevent them to enter one's body is much needed. The bacteria and viruses including COVID-19 travel via droplets expelled from one's mouth through coughing, talking, and breathing and remain in the air for a long time. An air purifier prevents these harmful particles to enter one's body.

SUMMARY OF THE INVENTION

The present invention is a personalized air purifier in combination with a mask to provide clean breathing air. The air purifier comprises of a small container, which can be attached to a belt or hang from the neck of a user. The container is preferably made of a light weight material and includes a bottom wall, side walls and a top opening adapted to house a plurality of chambers.

The filtering system of the personalized air purifier mask is a combination of wet filter, ionization filter, dehumidifier and UV LED disinfection system. The personalized forced air purifier mask is a multi-container air purifier comprising of a plurality of chambers placed one after another building the mask container. Each chamber is a tubular container including a rear wall, a front opening and side walls. The first chamber of the container is a filter chamber comprising of metal mesh bottom and side walls. The chamber is filled with multi-layer microfiber filter with strong absorbability and is wetted by water or ionized water.

The opening of the first chamber is covered by a mesh face plate. The filter is packed between the mesh face plate and the chamber which can be replaced after contaminated with clean filter. The mesh face plate allows the ambient air to enter into the container for purifying.

The second chamber of the container is an ionization chamber comprising of two layer of copper mesh plates on top and bottom side of the chamber and a layer of water absorbent material in between of the two layers of copper mesh plates. The ionization will take place by applying voltage between the two copper mesh layers.

The third chamber is a dehumidifier chamber which contains silica gel that absorbs the humidity of the air passing through the ionization chamber. The dehumidifier chamber is a replaceable mesh chamber that can be removed and heated to reactivate its dehumidifying capabilities for further moisture control. The dehumidifier chamber removes the moisture and improves the air quality.

The fourth chamber is a UV LED chamber which contains UV LED strips around the chamber. The range of UV LED strips are between 280 to 330 nanometers and with wide angle beam to kill possible bacteria and viruses in passing air. UV LED light provides rapid and effective inactivation of microorganisms through a physical process. In another embodiment the fourth chamber contains sounding LED strips. In another embodiment a shiny reflector is installed to reflect the beams and increase the efficiency.

The chambers are made of a lightweight material and placed one after another and assembled in a configuration that each one can individually be opened and the contents inside can be replaced.

A battery driven rotary blower at the exit of the container supplies the quality air and delivers it to a flexible hose to the face of the user. The blower sucks the ambient air through the chambers and exhausts a purified air and directs it through an outlet-port to a flexible hose.

A power source is provided on the container to control the operation of the chambers and the blower. The power source is a DC battery or rechargeable Li-Ion battery pack or other suitable batteries.

A control system is programmed to manage the operations of the personalized air purifier.

The contaminated air passes through the filter chamber and the pollution, dust and contaminants of the air is scrubbed by the filter. The air is diverted into the ionization chamber and is disinfected inside the chamber and is diverted into the dehumidifier chamber. The humidity of the air is balanced inside the chamber and diverted into the UV LED chamber to be disinfected from microorganisms. The purified air is being released into the flexible hose and carried towards the user's face.

The personalized air purifier can be attached to a person's belt using any different types of securing means such as a belt buckle, or it can be hung on a person's neck.

The air purifier of the present invention can also be used with a full-face cover mask having an opening in front of it to direct the exhaled air out of the mask. The mask is held onto the user's head by any type of strap, such as standard elastic straps.

The present invention can be used in hospitals to protect patients against pandemic air borne diseases. It can also be used in dusty areas to filter the air, which is essential especially for people with allergies or asthma.

The present invention can also be equipped with a container for medical solutions to treat a variety of diseases. Inhalation solutions are typically aqueous-based formulations and contain therapeutically active ingredients and can be used by the present invention.

The present invention can also be equipped with a container for applying personalized aromatic fluids and good smells for the particular use of the user in areas with undesirable smells.

It is therefore an object of the present invention to provide an air purifier mask which has a combination of filtering system of wet filter, ionization filter, dehumidifier and UV LED disinfection in one device to create a healthy inhale air for the user.

It is another object of the present invention to provide a portable air purifying mask, which is lightweight, non-expensive, easy to use and safe.

Other objects, features, and advantages of the present invention will be readily appreciated from the following description. The description makes reference to the accompanying drawings, which are provided for illustration of the preferred embodiment. However, such embodiments do not represent the full scope of the invention.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

FIG. 1A is a perspective view of the present invention with multiple air purifying chambers;

FIG. 1B is a perspective view of the present invention showing the multiple air purifying chambers;

DETAILED DESCRIPTION OF PREFERRED EMBODIMENTS

Figures 2, 3:
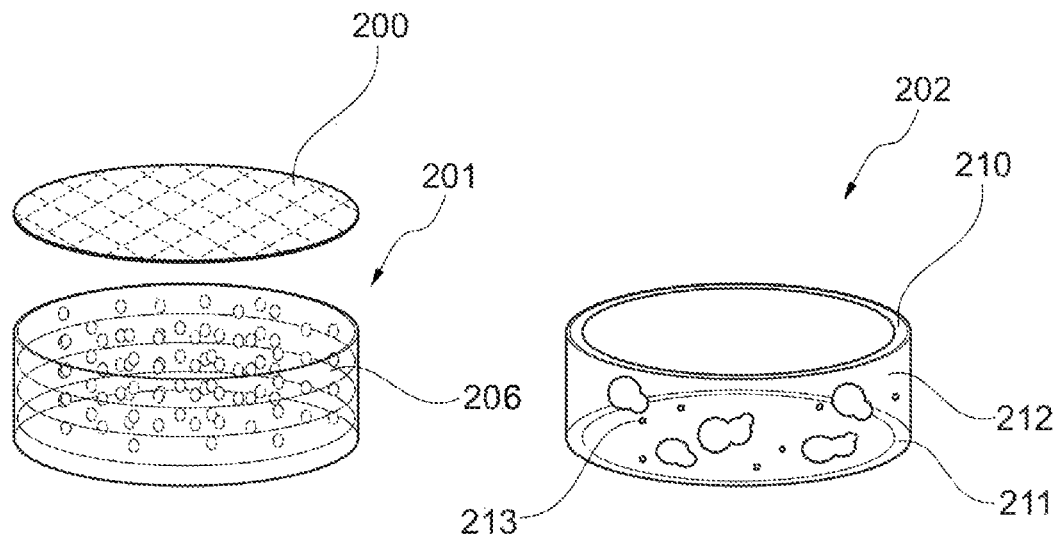
FIG. 2 is a perspective view of the filter chamber of the present invention according to FIG. 1A.
FIG. 3 is a perspective view of the ionization chamber of the present invention according to FIG. 1A.
Figures 4, 5:
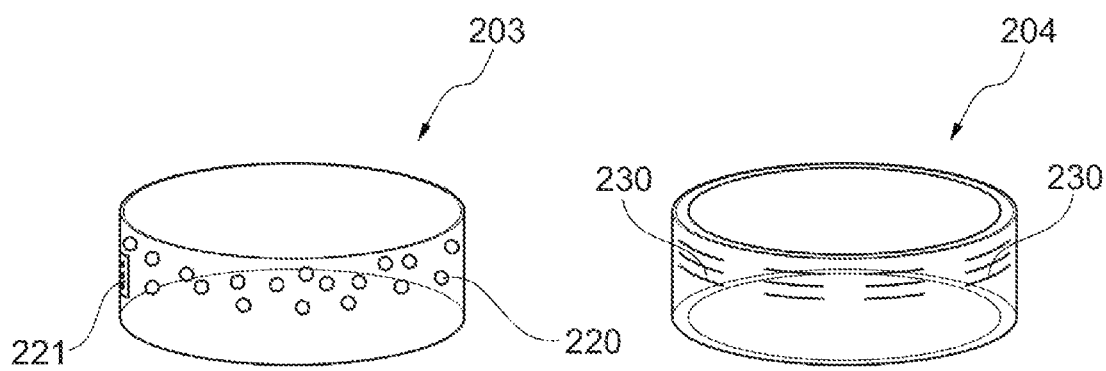
FIG. 4 is a perspective view of the dehumidifier chamber of the present invention according to FIG. 1A.
FIG. 5 is a perspective view of the UV LED chamber of the present invention according to FIG. 1A.
Figure 6A:
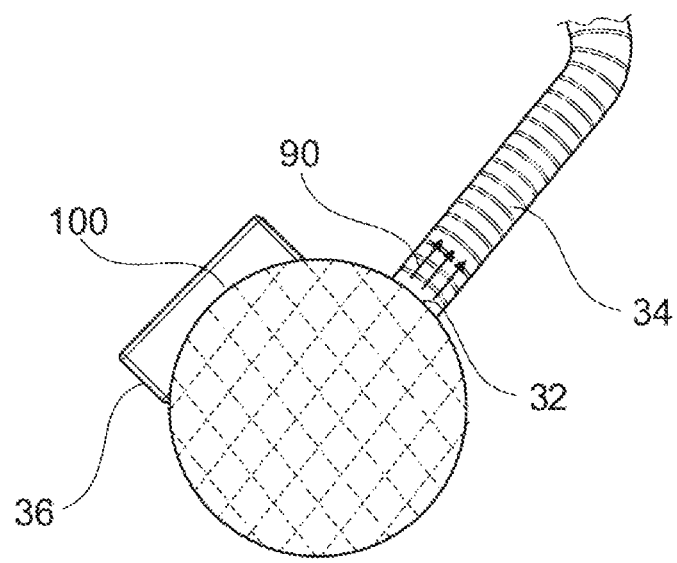
FIG. 6A is a top view of the present invention.
Figure 6B:
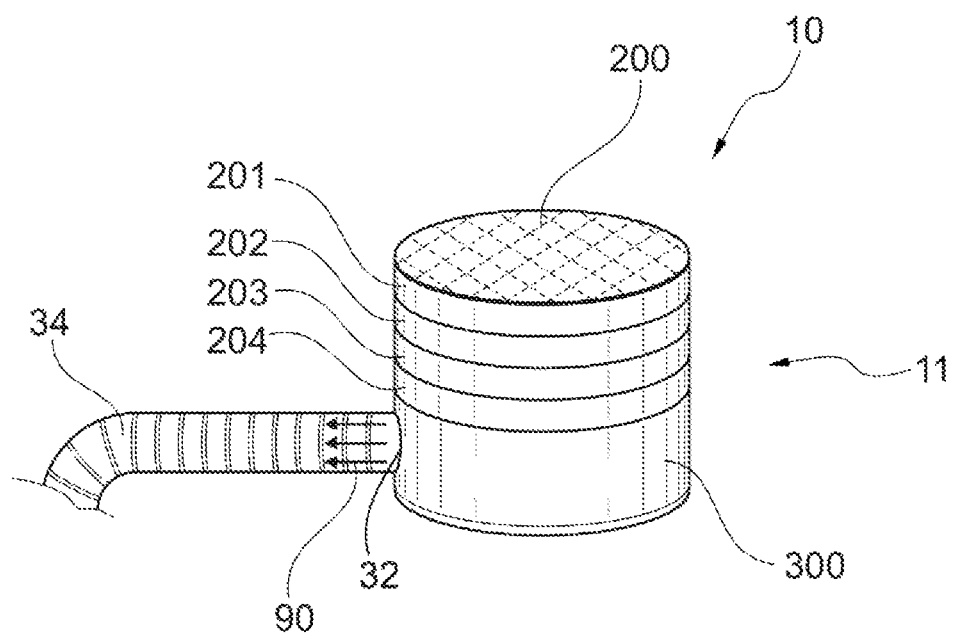
FIG. 6B is a perspective side view of the personalized air purifier connected to a flexible hose.

Referring to FIGS. 1 to 7, the personalized air purifier 10 comprising of a container 11, preferably made of a light weight material. The filtering system of the personalized air purifier 10 is a combination of wet filter, ionization filter, dehumidifier and UV LED disinfection system. The personalized air purifier 10 is a multi-container air purifier comprising of a plurality of chambers placed one after another building the container 11.

Each chamber is a tubular container including a rear wall, a front opening and a side wall. The first chamber of the container is a filter chamber 201 comprising of a metal or a plastic mesh bottom and side a wall. The chamber 201 is filled with multi-layer microfiber filter 206 with strong absorbability and is wetted by water or ionized water. In another embodiment, the chamber 201 can be filled with "gel soil water crystal beads" to absorb ionized water.

The opening of the top first chamber—the filter chamber—201 is covered by a face plate 200. The face plate 200 is a metal or plastic mesh plate to support the multi-layer microfiber filter 206 inside the chamber 201. The filter 206 (FIG. 2) is packed between mesh face plate 200 and the bottom and side walls of the chamber 201 which can be replaced after contaminated with clean filter 206. The mesh face plate 200 allows the ambient air 40 to enter into the container 11 for purifying. The contaminated air passes through the filter 206 and the pollution, dust and contaminants of the air are scrubbed by the filter 206. The purified air is then diverted into the second chamber. The face plate 200 is fastened onto the first chamber 201 by fastening means.

The second chamber of the container 11 is an ionization chamber 202. This chamber contains two layer of copper mesh 210-211 on top and bottom side of the chamber 202. A layer of water absorbent material 212, which is saturated of water is placed in between the two layers of copper mesh 210-211 inside the chamber 202 and acts as a wet filter. The ionization will take place by applying voltage between the two copper mesh layers 210-211 in the ionization chamber 202.

Copper mesh layers 210-211 act as electrodes and inject copper ions inside the water in the ionization chamber 202 and disinfect the air inside the ionization chamber 202. The copper mesh layers 210-211 are connected to the power source 100 of the system and release ions and act as an electrochemical treatment to kill the bacteria released from the ambient air 40. Each electrode is connected to a power source. The ions released in the absorbent material 212 kill the bacteria released from the ambient air through electrochemical process. The water 213 inside the ionization chamber 202 keeps the particles and kills the Bacteria and viruses passing through the ionization chamber 202. The ionization process in ionization chamber 202 and the amount of water inside the absorbent material 212 is controlled by the control system 36. The purified air is then released into the third chamber.

The third chamber is a dehumidifier chamber 203 which contains silica gel 220 that absorbs the humidity of the air passing through the ionization chamber 202. Silica gel is a natural dehumidifier. It absorbs moisture, reducing the humidity of its surrounding environment, is safe and highly effective. Silica gel can absorb up to 40% of its weight in water and it can be easily recharged with heat. The dehumidifier chamber 203 is a replaceable mesh chamber that can be removed and heated to reactivate its dehumidifying capabilities for further use moisture control.

The humidity of the output air is checked and controlled by the control system 36. An indicator 221 can be used to indicate that the silica gel 220 in the chamber 203 is saturated and needs to be reactivated. The indicator 221 can be a color changing or light indicator. To reactivate the silica gel 220 the entire dehumidifier chamber 203 can be removed and heated and replaced. In another embodiment the device 10 may include a self-heater to heat the dehumidifier chamber 203.

Dehumidifier chamber 203 helps to maintain healthy humidity levels in the air and cleanses the air of excess moisture and prevents mold, bacteria and other particulates from growing, all of which could lead to a variety of health issues, such as allergies, itchy throat and asthma. The dehumidifier chamber 203 removes the moisture and improves the air quality. The dehumidified air is then diverted into the UV LED chamber 204.

The fourth chamber is a UV LED chamber 204 which contains UV LED strips 230 around the chamber 204. The range of UV LED strips are 280-330 nanometers and kill possible bacteria or viruses in passing air 40. UV LED light provides rapid and effective inactivation of microorganisms through a physical process. When bacteria and viruses are exposed to the germicidal wavelengths of UV light, they are rendered incapable of reproducing and infecting.

A unique characteristic of UV light is that a specific range of its wavelengths, those between 200 and 300 nanometers, are categorized as germicidal. As air is forced through the chamber 204, it passes UV LED strips installed around the side wall of the chamber 204, which directly attempt to disinfect the air 40 by means of germicidal irradiation. There may be any number of strips in various configuration. In another embodiment, the fourth chamber 204 may contain sounding LED strips. In another embodiment a shiny reflector is installed to reflect the beams and increase the efficiency. Supplying voltage to run UV LED strips is controlled by the control system 36.

The chambers are made of a lightweight material and placed one after another and assembled in a configuration that each one can individually opened and the contents inside can be replaced. The chambers are fastened to each other in various methods and can be opened by twisting around an axis or sliding. In one embodiment the chambers are fitted within each other and held by frictional engagement.

The chambers are made of metal mesh to provide input and output openings which let the air pass through. In one embodiment to facilitate assembly of the chambers, the opening edges of the chambers have a bevel around the periphery of the opening and raised ribs which ensure a tight frictional fit with the adjacent chamber. In another embodiment the chambers are joined through frangible tabs. The chambers can be opened by twisting parts in opposite directions and then pull along the axis to open and gain access to the contents of the chambers.

In another embodiment a fifth filter chamber can be installed at the end of the multi container to absorb any remaining microbial.

A battery driven rotary blower 300 at the exit of the container 10 will supply the quality air 90 and deliver it through a flexible hose 34 to the face of the user by a mask 60. The blower 300 is attached to the fourth chamber 204 of the container 10 and sucks the ambient air 40 through the face plate 200 and exhausts a purified air 90 and directs it through an outlet-port 32 to the flexible hose 34. The flexible hose 34 is connected to the container-outlet-port 32 from one end and to a mask from another end.

A power source 100 is provided on the container 11 to control all the operation of the chambers and the blower 300. The power source is a DC battery or rechargeable Li-Ion battery pack or other suitable batteries.

The control system 36 of the device is programmed to control the following operations through a plurality of sensors located in the chambers:
control the ionization in ionization chamber;
check the amount of water inside the absorbent material;
check the humidity of the output air;
check the flow of the air inside the chambers, so that the air flow rate is set to 15-25 lit/min which is the human normal air needed. This is being done by a flow sensor and change the flow to 25 lit/min during inhale and 15 lit/min during exhale;
check the activation of the silica gel inside the dehumidifier chamber and indicate the activation time;
control the flow of the air by applying voltage to the blower;
supply voltage to run UV LEDs;
check the humidity of the output air;
check the flow of air by applying voltage to the blower, and
indicate if any of the critical parameters (UV light, air flow, humidity, ionization, etc.) fails.

The control system 36 has a control panel with indicators and switches thereon to control the operation of the device by the user.

The contaminated air 40 passes through the filter chamber 201 and the pollution, dust and contaminants of the air is scrubbed by the filter 206. The air is diverted into the ionization chamber 202 and is disinfected inside the chamber and is diverted into the dehumidifier chamber 203. The humidity of the air is balanced inside the chamber 203 and then diverted into the UV LED chamber 204 to be disinfected from microorganisms. The purified air 90 is then diverted into the air hose 34. The purified air 90 is then released into the flexible hose 34 through a container-outlet-port 32. The purified air is then carried towards the user's face.

Figure 7:
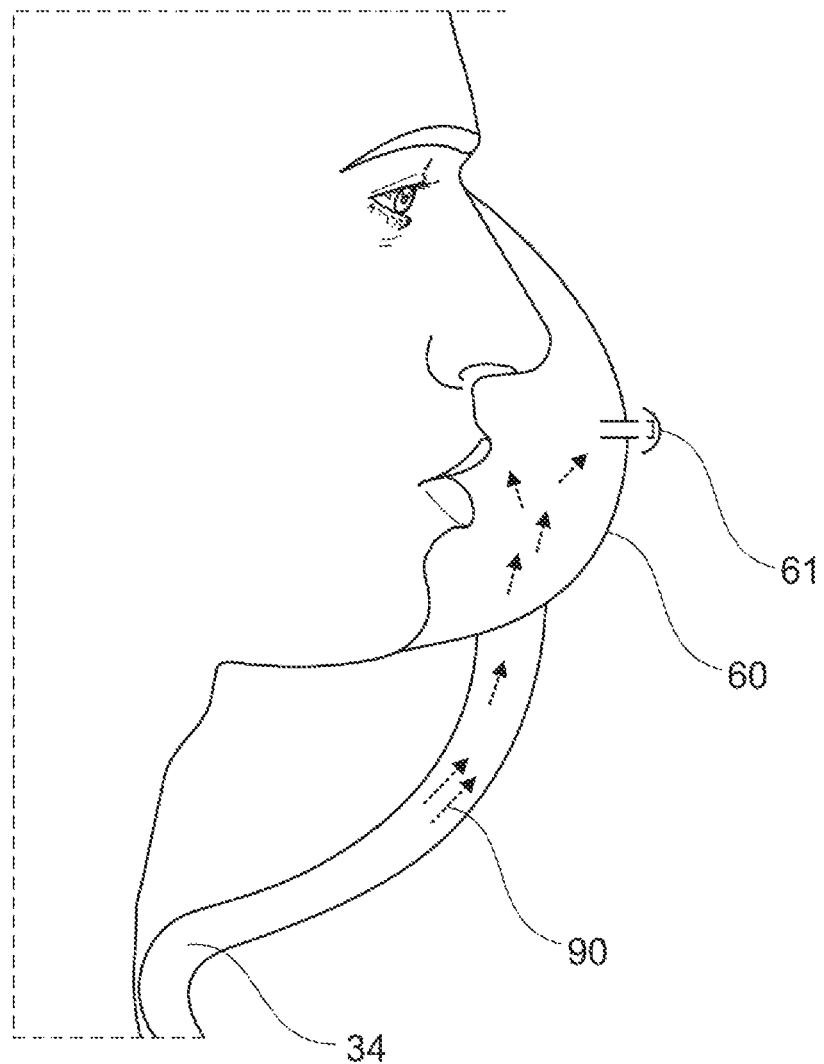
FIG. 7 is a perspective view of the mask portion of the present invention.

Referring to FIG. 7, air generating mask 60 has an opening 61 in front of it. This enables the user to inhale and exhale the forced purified air through the mask 60. Because the purified air is forced through the mask 60 and there is a continuous flow of purified air in and out of the mask, the unpurified air cannot enter the mask. The purified air 90 is directed into the mask 60 through the flexible hose 34 and the exhaled air is carried out of the mask 60 through the opening 61. The personalized air purifier 10 is made of a light weight material to be attached to a belt or hang from the neck of a user. The flexible hose 34 may comprise of rigid or resilient material or clear plastic material.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:
1. A personalized air purifier comprising:
a) a container having an inlet area and an outlet area, wherein the inlet area of the container is exposed to an ambient air, the container has a plurality of chambers placed respectively inside the container to purify an air passing through, and wherein the ambient air enters the plurality of chambers through a mesh face plate, each one of the plurality of chambers is a tubular container having a bottom wall, a removable top wall and side walls, each one of the plurality of chambers individually opens to replace a content,
b) the plurality of chambers comprises of,
   i. a filter chamber to purify the ambient air from pollution, dust and contaminants;
   ii. an ionization chamber to kill bacteria and viruses in the ambient air passing through said ionization chamber and provide an electrochemical treatment;
   iii. a dehumidifier chamber to help maintain healthy humidity levels in the air passing through said dehumidifier chamber and cleanse the air of excess moisture, and
   iv. a UV LED chamber to provide a rapid and effective inactivation of microorganisms and disinfect the air entering the UV LED chamber,
c) a blower attached to the outlet area to suck the ambient air into the filter chamber through the mesh face plate and passing through the ionization chamber, the dehumidifier chamber and the UV LED chamber and exhaust a purified air;
d) a power source for operation of the plurality of chambers and the blower;
e) a face mask to receive the purified air, wherein the purified air is directed into a flexible hose through an outlet port and into the face mask, allowing a user of the face mask to breath the purified air;

f) a control system to manage the operations of the personalized air purifier, whereby the ambient air passes through the filter chamber and the pollution, dust and contaminants of the ambient air is scrubbed and is diverted into the ionization chamber and is disinfected therein, the ambient air is diverted into the dehumidifier chamber to balance the moisture of the air inside the dehumidifier chamber and then diverted into the UV LED chamber to be disinfected from the microorganisms.

2. The personalized air purifier of claim 1, wherein the filter chamber has a metal mesh bottom, a side wall and a top opening, said top opening is covered by a metal mesh face plate, said filter chamber is filled with a replaceable multi-layer microfiber filter wetted by water or ionized water, wherein said multi-layer microfiber filter is packed between the metal mesh face plate, the metal mesh bottom and the side wall of the filter chamber, whereby the ambient air passes through the metal mesh face plate inside the filter chamber and passes through the multi-layer microfiber filter and the pollution, dust and contaminants of the air are scrubbed by the multi-layer microfiber filter and diverted into the ionization chamber for further purifying.

3. The personalized air purifier of claim 1, wherein the ionization chamber comprises of two layers of copper mesh plates on the top and bottom walls of the ionization chamber and a layer of water absorbent material in between of the two layers of copper mesh plates, whereby the two copper mesh layers act as electrodes and inject copper ions inside the water absorbent material and act as electrochemical treatment to disinfect the air entering the ionization chamber.

4. The personalized air purifier of claim 3, wherein the copper mesh layers are connected to the power source and the ionization will take place by applying voltage between the two copper mesh layers.

5. The personalized air purifier of claim 1, wherein the dehumidifier chamber is a replaceable mesh chamber and contains silica gel to absorb the humidity of the air passing through the ionization chamber, the dehumidifier chamber is capable to be removed and heated to reactivate its dehumidifying capabilities.

6. The personalized air purifier of claim 2, wherein the control system is configured to control the operations of the personalized air purifier through a plurality of sensors, the control system is programmed to:

a) control the ionization in the ionization chamber;
b) control the amount of the water or ionized water inside the replaceable multi-layer microfiber filter;
c) control the humidity of the purified air;
d) control an air flow rate inside the chambers by applying voltage to the blower;
e) control the activation of silica gel inside the dehumidifier chamber and indicate an activation time;
f) supply voltage to run UV LED strips in the UV LED chamber, and
g) indicate if any of the UV LED beams, air flow rate, humidity and ionization fail.

7. The personalized air purifier of claim 6, wherein the air flow rate is set to 15-25 lit/min which is the human normal air needed and change to 25 lit/min during an inhale and 15 lit/min during an exhale.

* * * * *